United States Patent [19]

Humphreys et al.

[11] Patent Number: 5,385,685
[45] Date of Patent: Jan. 31, 1995

[54] COMPOSITIONS COMPRISING GLYCEROGLYCOLIPIDS HAVING AN ETHER LINKAGE AS A SURFACTANT OR COSURFACTANT

[75] Inventors: Robert W. Humphreys, Oradell, N.J.; Anthony Hung, New City, N.Y.; Shang-Ren Wu, Mahwah, N.J.; Abid N. Khan-Lodhi, Hoole Chester, United Kingdom

[73] Assignee: Lever Brothers Company, Division of Conopco, Inc., New York, N.Y.

[21] Appl. No.: 981,977

[22] Filed: Nov. 25, 1992

Related U.S. Application Data

[63] Continuation-in-part of Ser. No. 816,437, Dec. 31, 1991, abandoned.

[51] Int. Cl.$^6$ ............................................. C11D 17/00
[52] U.S. Cl. .................... 252/174.17; 252/170; 536/4.1; 536/17.2; 514/844
[58] Field of Search .................... 252/170, 174.17, 550; 514/844; 536/4.1, 17.2

[56] References Cited

U.S. PATENT DOCUMENTS

| | | |
|---|---|---|
| 3,729,461 | 4/1973 | Pomeranz . |
| 4,011,169 | 3/1977 | Diehl et al. . |
| 4,804,497 | 2/1989 | Urfer et al. . |
| 4,859,589 | 8/1989 | Godfretsen et al. . |

FOREIGN PATENT DOCUMENTS

| | | |
|---|---|---|
| 0080855 | 6/1983 | European Pat. Off. . |
| 0232851 | 8/1987 | European Pat. Off. ............ 536/4.1 |
| 9304075 | 3/1993 | WIPO . |

OTHER PUBLICATIONS

Junichi Kobayashi, et al. "Hymenosulpghate, A Novel Sterol Sulphate" J. Chem. Soc. Perkin. Trans. 1 (1989) pp. 101–103.
Williams et al., "A New Class of Model Glycolipids", Archives of Biochemistry and Biophysics, vol. 195, No. 1, pp. 145–151 (Jun. 1979).
Coulon–Moulec, "Synthesis of Lipid Glycosides of Glucuronic Acid", Bull. Soc. Chem. Biol., vol. 49, No. 7, pp. 825–840 (1967).
Alvarez, et al., "High-resolution proton NMR characterization of seminolipid from bovine spermatozoa", J. Lipid Res., vol. 31, No. 6, pp. 1073–1081 (1990).
Baruah et al., "A Monoacyl Galactosylglcerol from Sonchus Arvensis", Phytochemistry, vol. 22, No. 8, pp. 1741–1744 (1983).
Kushwaha et al, "Survey of Lipids of a New Group of Extremely Halophilic Bacteria" Can. J. Microbiol. vol. 28 No. 12, pp. 1365–1372.

*Primary Examiner*—George Fourson
*Assistant Examiner*—C. Everhart
*Attorney, Agent, or Firm*—Ronald A. Koatz

[57] ABSTRACT

The present invention relates to detergent compositions comprising a glyceroglycolipid having one or two ether linkages for use as a surfactant or cosurfactant in the detergent compositions.

14 Claims, 2 Drawing Sheets

COMPOSITIONS COMPRISING GLYCEROGLYCOLIPIDS HAVING AN ETHER LINKAGE AS A SURFACTANT OR COSURFACTANT

CROSS REFERENCES

This is a continuation-in-part of Ser. No. 07/816,437 filed Dec. 31,1991, now abandoned.

BACKGROUND OF THE INVENTION

The present invention relates to novel detergent or novel personal product compositions comprising glyceroglycolipids having an ether linkage as surfactants or cosurfactants in the compositions. In particular, the glyceroglycolipid compounds are compounds having 1 to 4 saccharide units.

Natural glycolipids are known in the art and these structures have been elucidated. The term glycolipid refers to any of a class of lipids that, upon hydrolysis, yield a sugar (e.g., galactose or glucose), and a lipid (e.g. substituted glycerol group). One major class of these glycolipids belong to the glycero glycolipids, i.e., a, glycolipid based around a glycerol frame structure. For example, the compound may have a sugar structure at one end of the glycerol structure instead of an —OH group and an ester linkage at one or both of the other —OH groups that would normally be found on glycerol.

U.S. Pat. No. 3,729,461 to Pomeranz et al., for example, teaches mono- and di-galactosyl glyceride compounds isolated from wheat flour. On one end of the glycerol frame is found a sugar group (i.e., the mono- or di-saccharide group) and the two other OH groups normally found on a glycerol are esterified.

In Kobayashi et al., J. Chem Soc. Perkin., Trans. p. 101-103 (1989), there are again taught mono-and di-galactosyl diacylglycerols similar to chose taught in Pomeranz et al. Again, there is a sugar group on one end and a mono- or diester where the remaining two —OH groups on a glycerol would normally be found.

Other ester functionalized mono- and diacyl galactosylglycerols are taught in Baruah et al., Phytochemistry, 22(8):1741-1744 (1983) and in U.S. Pat. No. 4,859,589 to Godfretsen et al.

As mentioned above, the above references disclose only ester-functionalized glyceroglycolipids.

Williams et al. Archives of Biochemistry and Biophysics, 195(1):145-151 (1979) teach certain alkyl bionamide compounds which are formed by linking aldobionic acids to an alkylamine through an amide bond. The compounds of the invention contain no such amide bond.

U.S. Pat. No. 4,011,169 to Diehl et al. teaches enzyme containing compositions comprising certain aminated polysaccharides as stabilizing agents for the enzymes. First this reference relates to an amine linkage rather than an ether linkage. Further, it is clear from this reference that the polysaccharides used have at the very least 5 or more saccharide units and preferably, well over 100 (the application notes at column 7, line 50-52, that natural polysaccharides that are smaller than this are rare). Further there is a limitation as to the amount of elemental nitrogen to to the compound and it seems that compounds with fewer saccharide units would not meet this limitation.

A glyceroglycolipid containing an ether linkage (where the —OH group on the glycerol would normally be found) is disclosed in Coulon-Moulec, Bull. Soc. Chem. Biol., 49(7):825-840 (1967) and in Alvarez et al. , J. Lipid Res., 31(6) :1073-1081 (1990) .

These references are concerned, however, only with the synthesis of various lipid glycosides and contains absolutely no teaching or suggestion that glyceroglycolipids having an ether linkage can be used as surfactants or cosurfactants in detergent or personal product compositions.

EP No. 232,851-A (Assigned to National Starch) also appears to teach a glycceroglycolipid with an ether linkage. However, this reference is clearly concerned with compounds used as paper strength additives and neither teaches nor suggests that these compounds may be used as surfactants in detergent or personal product compositions.

U.S. Pat. No. 4,804,497 teaches a glycoside surfactant for enhancing the antistatic effects of certain quaternary ammonium surfactants. There is absolutely no teaching or suggestion that the surfactant can be used alone or in combination with other surfactants to enhance detergency.

Specifically although Table A at columns 5-6 talks about cleaning performance, there is no teaching of how results were reached or against what it was tested. This is not surprising since the reference is concerned with softening, not detergency and evaluates primary how the surfactant and cosurfactant affect static charge build up.

Finally, because the compounds of the invention are derived from naturally occurring carbohydrates, the use of these compounds can provide a source of renewable raw materials that are synthetically versatile and environmentally friendly.

Accordingly, it is an object of this invention to provide novel surfactants and cosurfactants derived from carbohydrates for use in detergent and personal product compositions. More particularly, it is an object of the invention to provide compositions comprising these biodegradable surfactants.

SUMMARY OF THE INVENTION

The present invention relates to detergent and personal product compositions comprising a glyceroglycolipid having one or two ether linkages for use as a surfactant or cosurfactant in the compositions. In particular the glyceroglycolipid has the following formula:

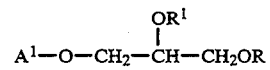

wherein $A^1$ is a saccharide, preferably having one to four saccharide units, more preferably a mono or disaccharide, and R or $R^1$ are the same or different and represent a hydrogen, a straight chained or branched, saturated or unsaturated hydrocarbon radical (including aryl, arene, etc.) having 1 to 24, preferably 6 to 18, carbons; or an acyl group except that R and $R^1$ cannot both be hydrogen (i.e. must be at least one ether linkage).

DETAILED DESCRIPTION OF THE INVENTION

Figure 1:
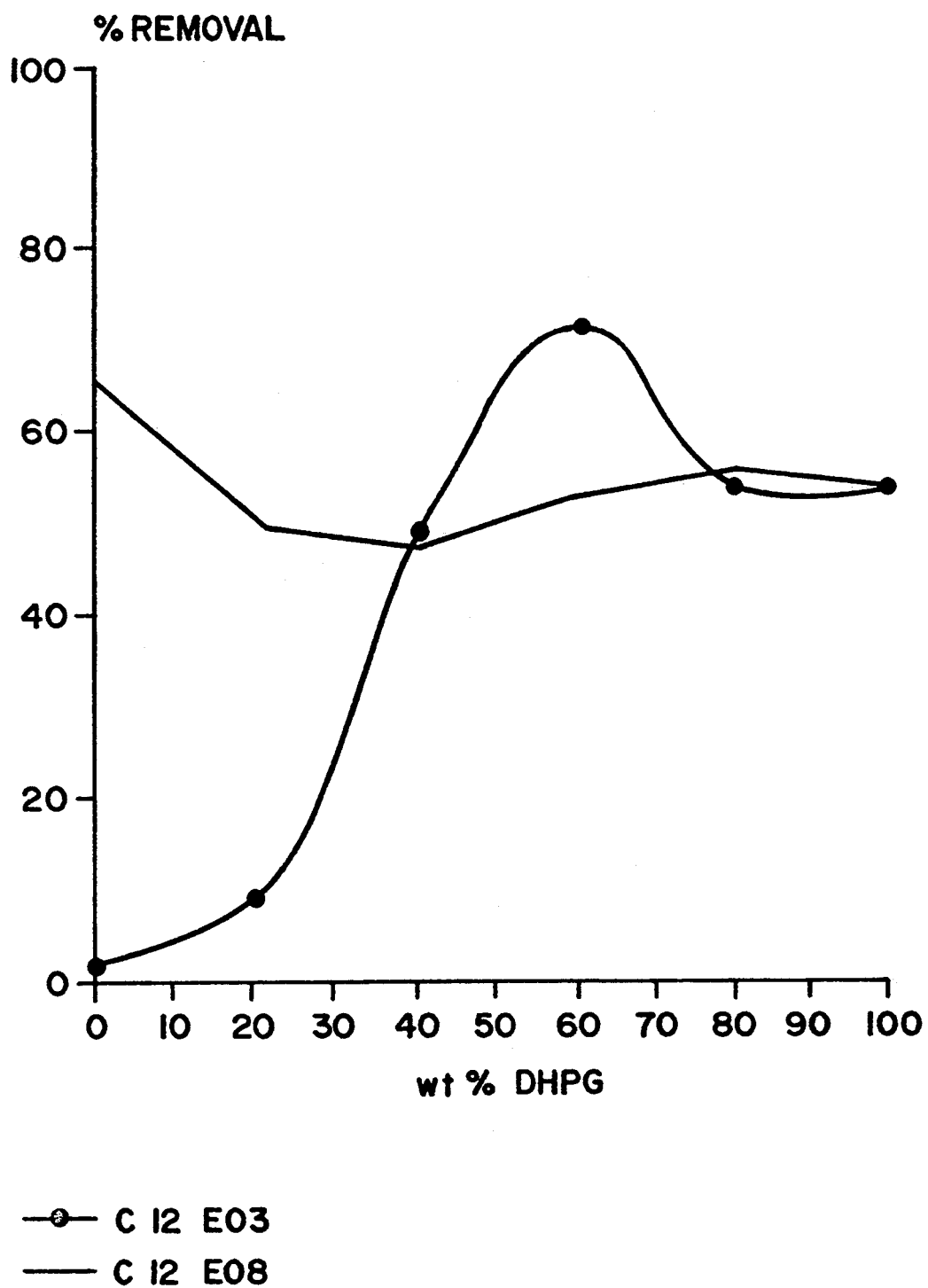
FIG. 1 is a graph showing oily soil (i.e., triolein) removal with various ratios of DHPG to $C_{12}EO_3$ and $C_{12}EO_8$.

The present invention provides detergent and personal product compositions comprising, as a surfactant or cosurfactant, a glyceroglycolipid compound having the structure set forth below:

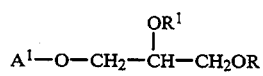

wherein $A^1$ is a saccharide, preferably having one to four saccharide units, more preferably a mono- or disaccharide, and most preferably a monosaccharide such as glucose or galactose; and R or $R^1$ are hydrogen, a branched or unbranched, saturated or unsaturated hydrocarbon radical having from about 1 to about 24, preferably from about 6 to about 18 carbons or an acyl group, except that R and $R^1$ cannot both be hydrogen at the same time.

In a preferred embodiment of the invention, $A^1$ is a monosaccharide and, in particular, is a galactoside (e.g., D-galactoside), $R^1$ is hydrogen and R is a $C_{12}$ alkyl chain.

These examples of compounds of the invention (having varying R or $A^1$ groups) are set forth below:

3-(butyloxy)-2-hydroxypropyl-β-D-Galactopyranoside
3-(pentyloxy)-2-hydroxypropyl-β-D-Galactopyranoside
3-(hexyloxy)-2-hydroxypropyl-β-D-Galactopyranoside
3-(heptyloxy)-2-hydroxypropyl-β-D-Galactopyranoside
3-(octyloxy)-2-hydroxypropyl-β-D-Galactopyranoside
3-(nonyloxy)-2-hydroxypropyl-β-D-Galactopyranoside
3-(decyloxy)-2-hydroxypropyl-β-D-Galactopyranoside
3-(dodecyloxy)-2-hydroxypropyl-β-D-Galactopyranoside
3-(tetradecyloxy)-2-hydroxypropyl-β-D-Galactopyranoside
3-(hexadecyloxy)-2-hydroxypropyl-β-D-Galactopyranoside
3-(octadecyloxy)-2-hydroxypropyl-β-D-Galactopyranoside
3-(eicosyloxy)-2-hydroxypropyl-β-D-Galactopyranoside
3-(docosyloxy)-2-hydroxypropyl-β-D-Galactopyranoside
3-(tetracosyloxy)-2-hydroxypropyl-β-D-Galactopyranoside
3-(hexenyloxy)-2-hydroxypropyl-β-D-Galactopyranoside
3-(decenyloxy)-2-hydroxypropyl-β-D-Galactopyranoside
3-(dodecenyloxy)-2-hydroxypropyl-β-D-Galactopyranoside
3-(tetradecenyloxy)-2-hydroxypropyl-β-D-Galactopyranoside
3-(hexadecenyloxy)-2-hydroxypropyl-β-D-Galactopyranoside
3-(octadecenyloxy)-2-hydroxypropyl-β-D-Galactopyranoside
3-(docosenyloxy)-2-hydroxypropyl-β-D-Galactopyranoside
3-(tetracosenyloxy)-2-hydroxypropyl-β-D-Galactopyranoside
3-(3-oxa-tridecyloxy)-2-hydroxypropyl-β-D-Galactopyranoside
3-(fluorododecyloxy)-2-hydroxypropyl-β-D-Galactopyranoside
3-(butyloxy)-2-hydroxypropyl-β-D-Glucopyranoside
3-(octyloxy)-2-hydroxypropyl-β-D-Mannopyranoside
3-(tetradecyloxy)-2-hydroxypropyl-β-D-lactoside
3-(octadecyloxy)-2-hydroxypropyl-β-D-maltoside
3-(octyloxy)-2-hydroxypropyl-β-D-galactotrioside
3-(dodecyloxy)-2-hydroxypropyl-β-D-cellotrioside

SYNTHESIS

The glyceroglycolipid of the invention is formed from a precursor having an epoxide group at the location where the ether linkage is formed and having a sugar group. The sugar may be protected or unprotected. An example of such a precursor would be the galactose epoxide compound having the structure:

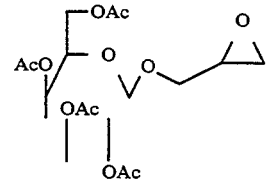

Once the protected epoxide galactose compound is obtained, this can be reacted with an alcohol ROH (wherein R represents the desired chain length of the alkyl group forming the ether linkage) desirably in the presence of a Lewis acid catalyst such as zinc chloride or stannic chloride; or in the presence of a cationic radical generator such as 2,3-dichloro-5,6-dicyano benzoquinone (ddq) to form the desired glyceroglycolipid with ether linkage.

The epoxide precursor used to form the desired surfactant can in turn be formed in a variety of ways.

For example, a galactose epoxide compound may be synthesized enzymatically via the hydrolysis of lactose in the presence of allyl alcohol and β-galactosidase to form a allyl-β-D-galactopyranoside which can then be protected and oxidized to the corresponding epoxide with m-chloroperoxybenzoic acid (m-CPBA) in dichloromethane. This type of reaction, which is taught in Nilsson, K.G.I., *Carbohydrate Research*, 180:53–59 (1988) is set forth below:

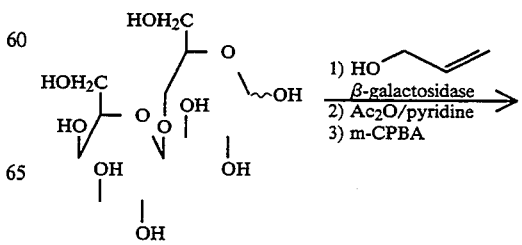

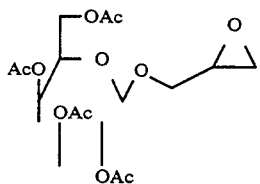

A chemical mode for preparation of the galactose epoxide involves the use of acetobromogalactose (2,3,4,6-tetra-O-acetyl-α-D-galactopyranosyl bromide) mixed with allyl alcohol with mercuric cyanide. This simple Koenigs-Knorr glycosydation affords the allyl-β-D-galactopyranoside tetraacetate in very good yield. Oxidation with peracide gives the protected epoxide sugar.

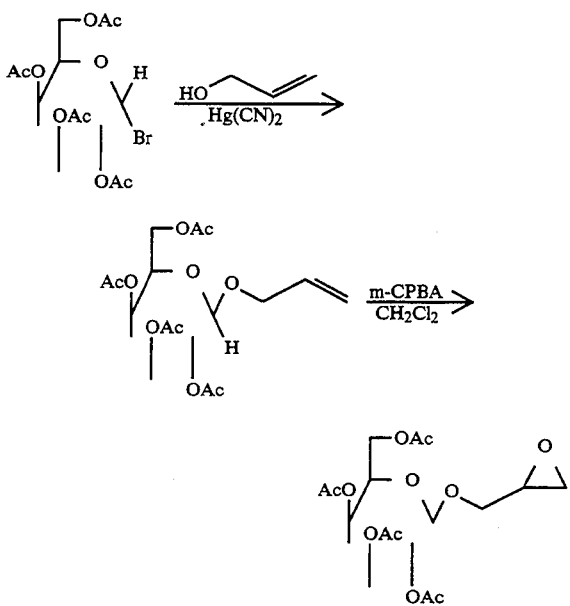

Once the epoxide precursor is formed, as discussed above, the epoxide ring is opened and OH groups are regenerated from the acetylated groups via hydrolysis.

COMPOSITIONS

The surfactants of the invention may be used in cleansing or detergent composition such as heavy duty liquid detergents (generally enzyme containing) or powdered detergents. Examples of liquid or powdered detergents are described in U.S. Pat. No. 4,959,179 to Aronson (for liquid detergent compositions) and U.S. Pat. No. 4,929,379 to Oldenburg et al. (for powdered detergent compositions), both of which are incorporated herein by reference.

The liquid detergent compositions of the invention may be built or unbuilt and may be aqueous or nonaqueous. The compositions generally comprise about 5%–70% by weight of a detergent active material and from 0% to 50% of a builder.

The composition may comprise 5–70% entirely the surfactant of the invention or it may comprise a mixture of surfactants wherein the surfactant of the invention comprises 40 to 80% of the mixture, preferably 50 to 70% of the mixture. The liquid detergent compositions of the invention may further comprise an amount of electrolyte (defined as any water-soluble salt) whose quantity depends on whether or not the composition is structured. By structured is meant the formation of a lamellar phase sufficient to endow solid suspending capability.

More particularly, while no electrolyte is required for a non-structured, non-suspending composition, at least 1%, more preferably at least 5% by weight and most preferably at least 15% by weight electrolyte is used. The formation of a lamellar phase can be detected by means well known to those skilled in the art.

The water-soluble electrolyte salt may be a detergency builder, such as the inorganic salt sodium tripolyphosphate or it may be a non-functional electrolyte such as sodium sulphate or chloride. Preferably, whatever builder is used in the composition comprises all or part of the electrolyte.

The liquid detergent composition generally further comprises enzymes such as proteases, lipases, amylases and cellulases which, when present, may be used in amounts from about 0.01 to 5% of the compositions. Stabilizers or stabilizer systems may be used in conjunction with enzymes and generally comprise from about 0.1 to 15% by weight of the composition.

The enzyme stabilization system may comprise calcium ion, boric acid, propylene glycol and/or short chain carboxylic acids. The composition preferably contains from about 0.01 to about 50, preferably from about 0.1 to about 30, more preferably from about 1 to about 20 millimoles of calcium ion per liter.

When calcium ion is used, the level of calcium ion should be selected so that there is always some minimum level available for the enzyme after allowing for complexation with builders, etc., in the composition. Any water-soluble calcium salt can be used as the source of calcium ion, including calcium chloride, calcium formate, calcium acetate and calcium propionate. A small amount of calcium ion, generally from about 0.05 to about 2.5 millimoles per liter, is often also present in the composition due to calcium in the enzyme slurry and formula water.

Another enzyme stabilizer which may be used is propionic acid or a propionic acid salt capable of forming propionic acid. When used, this stabilizer may be used in an amount from about 0.1% to about 15% by weight of the composition.

Another preferred enzyme stabilizer is polyols containing only carbon, hydrogen and oxygen atoms. They preferably contain from 2 to 6 carbon atoms and from 2 to 6 hydroxy groups. Examples include propylene glycol (especially 1,2 propanediol which is preferred), ethylene glycol, glycerol, sorbitol, mannitol and glucose. The polyol generally represents from about 0.5% to about 15%, preferably from about 1.0% to about 8% by weight of the composition.

The composition herein may also optionally contain from about 0.25% to about 5%, most preferably from about 0.5% to about 3% by weight of boric acid. The boric acid may be, but is preferably not, formed by a compound capable of forming boric acid in the composition. Boric acid is preferred, although other compounds such as boric oxide, borax and other alkali metal borates (e.g. sodium ortho-, meta- and pyroborate and sodium pentaborate) are suitable. Substituted boric acids (e.g., phenylboronic acid, butane boronic acid and a p-bromo phenylboronic acid) can also be used in place of boric acid.

On especially preferred stabilization system is a polyol in combination with boric acid. Preferably, the weight ratio of polyol to boric acid added is at least 1, more preferably at least about 1.3.

With regard to the detergent active, the detergent active material may be an alkali metal or alkanolamine soap or a 10 to 24 carbon atom fatty acid, including polymerized fatty acids, or an anionic, a nonionic, cationic, zwitterionic or amphoteric synthetic detergent material, or mixtures of any of these.

Examples of the anionic synthetic detergents are salts (including sodium, potassium, ammonium and substituted ammonium salts) such as mono-, di- and triethanolamine salts of 9 to 20 carbon alkylbenzenesulphonates, 8 to 22 carbon primary or secondary alkanesulphonates, 8 to 24 carbon olefinsulphonates, sulphonated polycarboxylic acids prepared by sulphonation of the pyrolyzed product of alkaline earth metal citrates, e.g., as described in British Patent specification, 1,082,179, 8 to 22 carbon alkylsulphates, 8 to 24 carbon alkylpolyglycol-ether-sulphates, -carboxylates and -phosphates (containing up to 10 moles of ethylene oxide); further examples are described in "Surface Active Agents and Detergents" (vol. I and II) by Schwartz, Ferry and Bergh. Any suitable anionic may be used and the examples are not intended to be limiting in any way.

Examples of nonionic synthetic detergents which may be used with the invention are the condensation products of ethylene oxide, propylene oxide and/or battalion oxide with 8 to 18 carbon alkylphenols, 8 to 18 carbon fatty acid amides; further examples of nonionics include tertiary amine oxides with 8 to 18 carbon alkyl chain and two 1 to 3 carbon alkyl chains. The above reference also describes further examples of nonionics.

The average number of moles of ethylene oxide and/or propylene oxide present in the above nonionics varies from 1-30; mixtures of various nonionics, including mixtures of nonionics with a lower and a higher degree of alkoxylation, may also be used.

The nonionic may also be a sugar amide such as a polysaccharide amide. Specifically, the surfactant may be one of the lactobionamides described in the Ser. No. 816,419 to Au et al., hereby incorporated by reference; or it may be a polyhydroxy sugar amide such as, for example, those described in U.S. Pat. No. 5,009,814 to Kelkenberg, hereby incorporated by reference into the subject application.

Examples of cationic detergents which may be used are the quaternary ammonium compounds such as alkyldimethylammonium halogenides.

Examples of amphoteric or zwitterionic detergents which may be used with the invention are N-alkylamine acids, sulphobetaines, condensation products of fatty acids with protein hydrolysates; but owing to their relatively high costs they are usually used in combination with an anionic or a nonionic detergent. Mixtures of the various types of active detergents may also be used, and preference is given to mixtures of an anionic and a nonionic detergent active. Soaps (in the form of their sodium, potassium and substituted ammonium salts) of fatty acids may also be used, preferably in conjunction with an anionic and/or nonionic synthetic detergent.

Builders which can be used according to this invention include conventional alkaline detergency builders, inorganic or organic, which can be used at levels from 0% to about 50% by weight of the composition, preferably from 1% to about 20% by weight, most preferably from 2% to about 8%.

Examples of suitable inorganic alkaline detergency builders are water-soluble alkalimetal phosphates, polyphosphates, borates, silicates and also carbonates. Specific examples of such salts are sodium and potassium triphosphates, pyrophosphates, orthophosphates, hexametaphosphates, tetraborates, silicates and carbonates.

Examples of suitable organic alkaline detergency builder salts are: (1) water-soluble amino polycarboxylates, e.g., sodium and potassium ethylenediaminetetraacetates, nitrilotriacetates and N-(2-hydroxyethyl)-nitrilodiacetates; (2) water-soluble salts of phytic acid, e.g., sodium and potassium phytates (see U.S. Pat. No. 2,379,942); (3) water-soluble polyphosphonates, including specifically, sodium, potassium and lithium salts of ethane-1-hydroxy-1,1-diphosphonic acid; sodium, potassium and lithium salts of methylene diphosphonic acid; and sodium, potassium and lithium salts of ethane-1,1,2-triphosphonic acid. Other examples include the alkali methnal salts of ethane-2-carboxy-1,1-diphosphonic acid hydroxymethanediphosphonic acid, carboxylidiphosphonic acid, ethane-1-hydroxy-1,1,2-triphosphonic acid, ethane-2-hydroxy-1,1,2-triphosphonic acid, propane-1,1,3,3-tetraphosphonic acid, propane-1,1,2,3-tetraphosphonic acid, and propane-1,2,2,3-tetraphosphonic acid; (4) water soluble salts of polycarboxylate polymers and copolymers as described in U.S. Pat. No. 3,308,067.

In addition, polycarboxylate builders can be used satisfactorily, including water-soluble salts of mellitic acid citric acid, and carboxymethyloxysuccinic acid and salts of polymers of itaconic acid and maleic acid. Specific polycarboxylate builders include DPA (dipicolinic acid) and ODS (oxydisuccinic acid). Certain zeolites or aluminosilicates can be used. One such aluminosilicate which is useful in the compositions of the invention is an amorphous water-insoluble hydrated compound of the formula $Na_x(yAlO_2.SiO_2)$, wherein x is a number from 1.0 to 1.2 and y is 1, said amorphous material being further characterized by a $Mg++$ exchange capacity of from about 50mg eq. $CaCO_3$/g. and a particle diameter of from about 0.01 micron to about 5 microns. This ion exchange builder is more fully described in British Pat. No. 1,470,250.

A second water-insoluble synthetic aluminosilicate ion exchange material useful herein is crystalline in nature and has the formula $Na_z[(AlO_2)_y.(SiO_2)]xH_2O$, wherein z and y are integers of at least 6; the molar ratio of z and y is in the range from 1.0 to about 0.5, and x is an integer from about 15 to about 264; said aluminosilicate ion exchange material having a particle size diameter from about 0.1 micron to about 100 microns; a calcium ion exchange capacity on an anhydrous basis of at least about 200 milligrams equivalent of $CaCO_3$ hardness per gram; and a calcium exchange rate on an anhydrous basis of at least about 2 grams/gallon/minute/gram. These synthetic aluminosilicates are more fully described in British Pat. No. 1,429,143.

In addition to the ingredients described hereinbefore, the preferred compositions herein frequently contain a series of optional ingredients which are used for the known functionality in conventional levels. While the detergent compositions are generally premised on aqueous, enzyme-containing detergent compositions, it is frequently desirable to use a phase regulant. This component together with water constitutes then the solvent matrix for the claimed liquid compositions. Suitable phase regulants are well-known in liquid detergent technology and, for example, can be represented by hydrotropes such as salts of alkylarylsulfonates having up to 3 carbon atoms in the alkylgroup, e.g., sodium, potassium, ammonium and ethanolamine salts of xylene-, toluene-, ethylbenzene-, cumene-, and isopropylbenzene sulfonic acids. Alcohols may also be used as phase regulants. This phase regulant is frequently used in an amount from about 0.5% to about 20%, the sum of phase regulant and water is normally in the range from 35% to 65%.

The preferred compositions herein can contain a series of further optional ingredients which are mostly used in additive levels, usually below about 5%. Examples of the like additives include: polyacids, suds regulants, opacifiers, antioxidants, bactericides, dyes, perfumes, brighteners and the like.

The beneficial utilization of the claimed compositions under various usage conditions can require the utilization of a suds regulant. While generally all detergent suds regulants can be utilized, preferred for use herein are alkylated polysiloxanes such as dimethylpolysiloxane, also frequently termed silicones. The silicones are frequently used in a level not exceeding 0.5%, most preferably between 0.01% and 0.2%.

It can also be desirable to utilize opacifiers inasmuch as they contribute to create a uniform appearance of the concentrated liquid detergent compositions. Examples of suitable opacifiers include: polystyrene commercially known as LYTRON 621 manufactured by Monsanto Chemical Corporation. The opacifiers are frequently used in an amount from 0.3% to 1.5%.

The compositions herein can also contain known antioxidants for their known utility, frequently radical scavengers in the art established levels, i.e., 0.001% to 0.25% (by reference to total composition).

When the liquid composition is an aqueous composition, the balance of the formulation consists of an aqueous medium. When it is in the form of a nonaqueous composition, the above ingredients make up for the whole formulation (a nonaqueous composition may contain up to 5% water).

An ideal liquid detergent composition might contain (all percentages by weight):
(1) 5-70% detergent active system;
(2) 0-50% builder;
(3) 0-40% electrolyte
(4) 0.01-5% enzyme;
(5) 0.1-15% enzyme stabilizer;
(6) 0-20% phase regulant; and
(7) remainder water and minors The detergent composition of the invention might also be a powdered detergent composition.

Such powdered compositions generally comprise from about 5-40% of a detergent active system which generally consists of an anionic, a nonionic active, a fatty acid soap or mixtures thereof; from 20-70% of an alkaline buffering agent; up to about 40% builder and balance minors and water.

The alkaline buffering agent may be any such agent capable of providing a 1% product solution with a pH of above 11.5 or even 12. Advantageous alkaline buffering agents are the alkalimetal silicates, as they decrease the corrosion of metal parts in washing machines, and in particular sodium orthometa- or di-silicates, of which sodium metasilicate is preferred. The alkaline buffering agent is present in an amount of from 0 to 70% by weight, preferably from 0 to 30% by weight.

In addition the compositions of the invention can and normally will contain detergency builders in an amount of up to 40% by weight and preferably from 5 to 25% by weight of the total composition.

Suitable builders include sodium, potassium and ammonium or substituted ammonium pyro- and tri-polyphosphates, -ethylene diamine tetraacetates, -nitrilotriacetates, -etherpolycarboxylates, -citrates, -carbonates, -orthophosphates, -carboxymethyloxysuccinates, etc. Specific builders include DPA and ODS. Also less soluble builders may be included, such as e.g., an easily dispersible zeolite. Particularly preferred are the polyphosphate builder salts, nitrilotriacetates, citrates, carboxymethyloxysuccinates and mixtures thereof.

Other conventional materials may be present in minor amounts, provided they exhibit a good dissolving or dispersing behavior; for example sequestering agents, such as ethylenediamine tetraphosphonic acid; soil-suspending agents, such as sodiumcarboxymethylcellulose, polyvinylpyrrolidone or the maleic anhydride/vinylmethylether copolymer, hydrotropes; dyes; perfumes; optical brighteners; alkali-stable enzymes; germicides; anti-tarnishing agents; lather depressants; fabric softening agents; oxygen- or chlorine-liberating bleaches, such as dichlorocyanuric acid salts or alkalimetal hypochlorides.

The remainder of the composition is water.

An ideal powdered detergent composition might contain the following (all percentages by weight):
(1) 5-40% detergent active system;
(2) 0-40% builder;
(3) 0-30% buffer salt;
(4) 0-30% sulfate;
(5) 0-20% bleach system;
(6) 0-4% enzyme; and
(7) Minors plus water to 100%

The surfactants of the invention may also be used in personal product compositions such as, for example, soap bar compositions, facial or body cleansing compositions, shampoos for hair or body, conditioners, cosmetic compositions or dental compositions.

In one embodiment of the invention, the surfactant of the invention may be used, for example, in a toilet bar (i.e., soap and/or detergent bar) formulation.

Typical toilet bar compositions are those comprising fatty acid soaps used in combination with a detergent other than fatty acid soap and free fatty acids. It should be noted that the composition may comprise no fatty acid soap and may be based on actives other than fatty acid soap. Mildness improving salts, such as alkali metal salt or isethionate, are also typically added. In addition other ingredients, such as germicides, perfumes, colorants, pigments, suds-boosting salts and anti-mushing agents may also be added.

Fatty acid soaps are typically alkali metal or alkanol ammonium salts of aliphatic alkane or alkene monocarboxylic acids. Sodium, potassium, mono-, di- and triethanol ammonium cations, or combinations thereof, are suitable for purposes of the invention.

The soaps are well known alkali metal salts of natural or synthetic aliphatic (alkanoic or alkenoic) acids having about 8 to 22 carbons, preferably 12 to about 18 carbons.

Examples of soap which may be used may be found in U.S. Pat. No. 4,695,395 to Caswell et al. and U.S. Pat. No. 4,260,507 (Barrett), both of which are incorporated herein by reference.

In a soap-based bar, fatty acid soaps will generally comprise greater than 25% of the composition, generally from 30–95%. Preferably, the amount of soap will range from 40% to 70% by weight of the composition. In a bar-based on other actives, soap may comprise 0–50% by weight. In general, $C_8$ to $C_{24}$ fatty acid comprises 5–60% of the composition.

The compositions will also generally comprise a non-soap detergent which is generally chosen from anionic, nonionic, cationic, zwitterionic or amphoteric synthetic detergent materials or mixtures thereof. These surfactants are all well known in the art and are described, for example, in U.S. Pat. Nos. 4,695,395 and 4,260,507 discussed above. One preferred non-soap anionic is a $C_8$–$C_{22}$ akyl isethionate. These ester may be prepared by the reaction between alkali metal isethionate and mixed aliphatic fatty acids having from 8 to 22 carbons. The non-soap actives may comprise from 0 to 50% of the composition.

A certain amount of free fatty acids of 8 to 22 carbons are also desirably incorporated into soap compositions to act as superfatting agents or as skin feel and creaminess enhancers. If present, the free fatty acids comprise between 1 and 15% of the compositions.

A preferred mildness improving salt which may be added to soap compositions is a simple unsubstituted sodium isethionate. This may be present as 0.1 to 50% of the composition, preferably 0.5% to 25%, more preferably 2% to about 15% by weight. Other mildness co-actives which may be used include betain compounds or ether sulphates. These also may be present at 0.1 to 50% of the composition, preferably 0.5% to 25%.

The sulfate ester surfactant may comprise 0.01 to 45% by weight of the composition (as the monoester), preferably 25% to 40%, and 0.01% to 10% of the composition (as the diester), preferably 0.01% to 5%.

Other optional ingredients which may be present in soap bar compositions are moisturizers such as glycerin, propylene glycol, sorbitol, polyethylene glycol, ethoxylated or methoxylated ether of methyl glucose etc; water-soluble polymers such as collagens, modified cellulases (such as Polymer JR ®), guar gums and polyacrylates; sequestering agents such as citrate, and emollients such as silicones or mineral oil. Another useful set of ingredients are various cosurfactants and non-soap detergents.

In a second embodiment of the invention, the glycerol frame surfactant with ether linkage of the invention may be present in a facial or body cleansing composition. Examples of such cleaning compositions are described, for example, in U.S. Pat. No. 4,812,253 to Small et al. and U.S. Pat. No. 4,526,710 to Fujisawa, both of which are hereby incorporated by reference.

Typically, cleansing compositions will comprise a fatty acid soap together with a non-soap surfactant, preferably a mild synthetic surfactant. Cleaning compositions will also generally include a moisturizer or emollient and polymeric skin feel and mildness aids. The compositions may further optionally include thickener (e.g. magnesium aluminum silicate, carbopol), conditioners, water soluble polymers (e.g. carboxymethyl cellulose), dyes, hydrotropes brighteners, perfumes and germicides.

The fatty acid soaps used are such as those described above in uses in toilet bar formulations. These soaps are typically alkali metal or alkanol ammonium salts of aliphatic or alkene monocarboxylic salts. Sodium, potassium, mono-, di- and triethanol ammonium cations, or combinations thereof are suitable. Preferred soaps are 8 to 24 carbon half acid salts of, for example, triethanolamine.

Surfactants can be chosen from anionic, nonionic, cationic, zwitterionic or amphoteric materials or mixtures thereof such as are described in U.S. Pat. No. 4,695,395 mentioned above, or in U.S. Pat. No. 4,854,333 to Inman et al, hereby incorporated by reference.

Moisturizers are included to provide skin conditioning benefits and improve mildness. This term is often used as synonymous with emollient and is then used to describe a material which imparts a smooth and soft feeling to skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanolin alcohol (e.g., Solulan-75).

Preferred moisturizers are coco and tallow fatty acids. Some other preferred moisturizers are the nonoclusive liquid water soluble polyols and the essential amino acid compounds found naturally in the skin.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEa.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—a Critical Evaluation," by J. Mausner, Cosmetics & Toiletries, May 1981, incorporated herein by reference.

The polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits.

The amount of polymeric skin feel and mildness aids found useful in the composition of the present invention is from about 0.01% to about 5%, preferably from about 0.3% to about 4%. In bar compositions with less than 5.5% soap, the polymer is used at a level of 2% to 5%, preferably 3% or more.

Other types of high molecular weight polymeric skin feel and skin mildness aids, such as nonionic guar gums, Merquats 100 and 550, made by Merck & Co, Inc.; Jaguar C-14-S made by Stein Hall; Mirapol a15 made by Miranol Chemical Company, Inc.; and Galactasol 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Corp. A preferred nonionic hydroxypropyl guar gum material is Jaguar® HP-60 having molar substitution of about 0.6. Another class of useful nonionics is the cellulosic nonionic polymers, e.g., HEC and CMC.

The cationic polymers employed in this invention also provide a desirable silky, soft, smooth in-use feeling. The preferred level for this invention is 0.1-5% of the composition. There is reason to believe that the positively charged cationic polymers can bind with negatively charges sites on the skin to provide a soft skin feel after use. Not to be bound by any theory, it is believed that the greater the charge density of the cationic polymer, the more effective it is for skin feel benefits.

Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok®300 and 400 made by Staley, Inc.

A more complete list of cationic polymers useful in the present invention is described in U.S. Pat. No. 4,438,095, to Grollier/allec, issued Mar. 20, 1984, incorporated herein by reference. Some of the more preferred cationics are listed in Col. 3, Section 2; Col. 5, section 8; Col. 8, section 10; and Col. 9, lines 10-15 of the Grollier/allec patent, incorporated herein by reference.

In a third embodiment of the invention, the surfactant of the invention may be used, for example, in a shampoo. Examples of such compositions are described in U.S. Pat. No. 4,854,333, to Inman and U.S. Pat. No. 4,526,710 to Fujisawa, both of which are hereby incorporated by reference.

The shampoo compositions which may be used typically comprise a surfactant selected from any one of a wide variety of surfactants known in the art (such as those described in U.S. Pat. No. 4,854,333, incorporated herein by reference).

Synthetic anionic surfactants, for example can be exemplified by the alkali metal salts of organic sulfuric reaction products having in their molecular structure an alkyl radical containing from about 8-22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols (C8-C18 carbon atoms), sodium coconut oil fatty acid monoglyceride sulfates and sulfonates; sodium or potassium salts of sulfuric acid esters of the reaction product of about 1 mole of a higher fatty alcohol (e.g., tallow or coconut oil alcohols) and from about 1 to about 12 moles of ethylene oxide; sodium or potassium salts of alkyl phenol ethylene oxide ether sulfate with from about 1 to about 10 units of ethylene oxide per molecule and in which the alkyl radicals contain from about 8 to about 12 carbon atoms; sodium alkyl glyceryl ether sulfonates; the reaction product of fatty acids having from 10 to about 22 carbon atoms esterified with isethionic acid and neutralized with sodium hydroxide; and water soluble salts of condensation products of fatty acids with sarcosine.

Examples of amphoteric surfactants which can be used in the compositions of the present invention are those broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate; sodium 3-dodecylaminopropane sulfonate; N-alkyltaurines, such as the one prepared by reacting dodecylamine with sodium isethionate according to the teaching of U.S. Pat. No. 2,658,072; N-higher alkyl aspartic acids, such as those produced according to the teaching of U.S. Pat. No. 2,438,091; and the products sold under the trade name "Miranol" and described in U.S. Patent No. 2,528,378. The shampoo compositions may additionally comprise a compound considered useful for treating dandruff, e.g. selenium sulfide.

The compositions all may also optionally comprise a suspending agent, for example, any of several acyl derivative materials or mixtures thereof. Among these are ethylene glycol esters of fatty acids having 16 to 22 carbons. Preferred suspending agents include ethylene glycol stearates, both mono- and distearate. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmitate), glyceryl esters (e.g. glyceryl distearate), and long chain esters of long chain alkanol amides (e.g., stearamide DEA distearate, stearamide MEA stearate).

Still other suitable suspending agents are alkyl (16 to 22 carbon) dimethyl amine oxides, such as stearyl dimethyl amine oxide. If the compositions contain an amine oxide or a long chain acyl derivative as a surfactant, these components may also provide the suspending function and additional suspending agent may not be needed.

Xanthan gum is another agent used to suspend, for example, selenium sulfide which may be in the present compositions. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. Supplemental information on these agents is found in Whistler, Roy L. (Editor), Industrial Gums—Polysaccharides and Their Derivatives New York: Academic Press, 1973. Kelco, a Division of Merck & Co., Inc., offers xanthan gum as Keltrol®.

A particularly preferred suspending system comprises a mixture of xanthan gum, present at a level of from about 0.05% to about 1.0%, preferably from about 0.2% to about 0.4%, of the compositions, together with magnesium aluminum silicate ($Al_2Mg_8Si_2$), present at a level of from about 0.1% to about 3.0%, preferably from about 0.5% to about 2.0%, of the compositions. Magnesium aluminum silicate occurs naturally in such smectite minerals as colerainite, saponite and sapphire. Refined magnesium aluminum silicates useful herein are readily available, for example as veegum, manufactured by R. T. Vanderbilt Company, Inc. Mixtures of suspending agents are also suitable for use in the compositions of this invention.

Other useful thickening agents are the cross-linked polyacrylates such as those manufactured by B. F. Goodrich and sold under the Carbopol® tradename.

Another optional component for use in the present compositions is an amide. The amide used in the present compositions can be any of the alkanolamides of fatty acids known for use in shampoos. These are generally mono- and diethanolamides of fatty acids having from about 8 to 24 carbon atoms. Preferred are coconut monoethanolamide, lauric diethanolamide and mixtures thereof. The amide is present at a level of from about 1% to about 10% of the compositions.

The compositions may also contain nonionic polymer material which is used at a low level to aid in dispersing particles. The material can be any of a large variety of types including cellulosic materials such as hydroxypropyl methyl cellulose, carboxymethyl cellulose, hydroxyethyl cellulose and sodium carboxymethyl cellulose as well as mixtures of these materials.

Other materials include alginates, polyacrylic acids, polyethylene glycol and starches, among many others. The nonionic polymers are discussed in detail in *Industrial Gums*, edited by Roy L. Whistler, academic Press, Inc., 1973, and *Handbook of Water-Soluble Gums and Resins*, edited by Robert L. Davidson, McGraw-Hill, Inc., 1980. Both of these books in their entirety are incorporated herein by reference.

When included, the nonionic polymer is used at a level of from about 0.001% to about 0.1%, preferably from about 0.002% to about 0.05%, of the composition. Hydroxypropyl methyl cellulose is the preferred polymer.

Another suitable optional component useful in the present compositions is a nonvolatile silicone fluid.

The nonvolatile silicone fluid may be either a polyalkyl siloxane, a polyaryl siloxane, a polyalkylarly siloxane or a polyether siloxane copolymer and is present at a level of from about 0.1% to about 10.0%, preferably from about 0.5% to about 5.0%. Mixtures of these fluids may also be used and are preferred in certain executions. The dispersed silicone particles should also be insoluble in the shampoo matrix. This is the meaning of "insoluble" as used herein.

The essentially nonvolatile polyalkyl siloxane fluids that may be used include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The siloxane viscosity can be measured by means of a glass capillary viscometer as set forth in Dow Corning Corporate Test Method CTM0004, Jul. 20, 1970. Preferably the viscosity of the these siloxanes range from about 350 centistokes to about 100,000 centistokes.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in U.S. Pat. No. 2,826,551, Geen; U.S. Pat. No. 3,946,500, Jun. 22, 1976, Drakoff; U.S. Pat. No. 4,364,837, Pader; and British Patent 849,433, Woolston. All of these patents are incorporated herein by reference. Also incorporated herein by reference is Silicon compounds, distributed by Petrarch Systems, Inc., 1984. This reference provides a very good listing of suitable silicone materials.

Another silicone material useful is silicone gum. Silicone gums are described by Petrarch and others including U.S. Pat. No. 4,152,416, May 1, 1979, Spitzer, et al., and Noll, *Chemistry and Technology of Silicones*, New York, academic Press, 1968. Useful silicone gums are also described in General Electric Silicone Rubber Product Data Sheets SE 30, SE 33, SE 54 and SE 76. all of these references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer, and mixtures thereof. Mixtures of silicone fluids and silicone gums are also useful herein.

The shampoos herein can contain a variety of other nonessential optional components suitable for rendering such compositions more formulatable, or aesthetically and/or cosmetically acceptable. Such conventional optional ingredients are well-known to those skilled in the art and include, e.g., preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers, such as block polymers of ethylene oxide and propylene oxide such as Pluronic F88 offered by BaSa Wyandotte, sodium chloride, sodium sulfate, propylene glycol, and ethyl alcohol; pH adjusting agents, such as citric acid, succinic acid, phosphoric acid, sodium hydroxide, sodium carbonate; perfumes; dyes; and sequestering agents, such as disodium ethylenediamine tetraacetate. Such agents generally are used individually at a level of from about 0.01% to about 10%, preferably from about 0.5% to about 5.0%, of the composition.

A typical shampoo composition may comprise (percentages by weight):
(1) 5–15% active of invention
(2) 0–10% anionic coactive;
(3) 0–10% amphoteric coactive;
(4) 0–5% lauramide MEA;
(5) 0–5% thickener;
(6) 0–2% fragrance;
(7) 0–1% preservative; and
(8) remainer water.

In a fourth embodiment of the invention, the surfactant of the invention may be used in a conditioner composition such as is taught and described in U.S. Pat. No.

4,913,828 to Caswell et al. which is hereby incorporated by reference.

More particularly, conditioner compositions are those containing a conditioning agent (e.g. alkylamine compounds) such as those described in U.S. Pat. No. 4,913,828.

A typical conditioner composition may comprise (percentages by weight):

(a) 1–98% surfactant of invention, preferably 10–60% (or 1–98% or 10–60% surfactant mixture comprising the surfactant of the invention and wherein cosurfactant(s) are selected from the group consisting of anionics, nonionics, ampholytics, zwitterionics and cationics);
(b) 0–80% builder (e.g., polycarboxylates);
(c) 0–10% chelating agent (e.g., amino carboxylates);
(d) 0–5% soil release agent (e.g., derivative of hydro)of ether cellulosic polymers);
(e) 0–5% antiredeposition agent (e.g., ethoxylated anionics);
(f) 0–2% enzymes (e.g., protease);
(g) 0.1–20% conditioning agent (e.g., cationic surfactant);
(h) 0.1–10% stabilizer for conditioner (e.g., clay or polysaccharide gum);
(i) water and minors to 100%.

If formulated as conditioner shampoos, the composition may comprise:

(a) 5–60% surfactant (wholly surfactant of invention or comprising the surfactant of invention);
(b) 1–60% conditioner;
(c) 0–20% preservative (e.g., benzyl alcohol);
(d) 0–16% thickener (e.g., diethanolamide); and
(e) remainder water and minors.

In a fifth embodiment of the invention, the surfactant may be used in a cosmetic composition, such as is taught and is described in EP 0,371,803.

Such compositions generally comprise thickening agents, preservatives and further additions.

The composition may comprise polymer thickener in an amount sufficient to adjust the viscosity of the composition, so as to facilitate dispensing it conveniently onto the body surface.

Examples of polymer thickeners include: anionic cellulose materials, such as sodium carboxy methyl cellulose; anionic polymers such as carboxy vinyl polymers, for example, Carbomer 940 and 941; nonionic cellulose materials, such as methyl cellulose and hydroxy propyl methyl cellulose; cationic cellulose materials, such as Polymer JR 400; cationic gum materials, such as Jaguar C13 S; other gum materials such as gum acacia, gum tragacanth, locust bean gum, guar gum and carrageenan; proteins, such as albumin and protein hydrolysates; and clay materials, such as bentonite, hectorite, magnesium aluminum silicate, or sodium magnesium silicate.

Generally, the thickening agent may comprise from 0.05 to 5%, preferably 0.1 to 1% by weight of the composition.

The composition according to the invention can also optionally comprise a preservative to prevent microbial spoilage.

Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitropropane-1, 3-diol, phenoxyethanol, dibromodicyanobutane, formalin and Tricolsan. The amount of chemical preservative optionally to be incorporated in the composition according to the invention will generally be from 0.05 to 5%, preferably from 0.01 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, sufficient should be incorporated in the composition according to the invention to reduce the water activity from 1 to <0.9, preferably to <0.85 and most preferably <0.8, the lowest of these values being that at which yeasts, molds and fungi will not proliferate.

The composition can also contain other optional adjuncts, which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1, 2-diol, butane-1.3 diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid isopropyl linoleate, lauryl lactate, myristyl lactate, decyl oleate, myristyl myristate;

Propellants, such as trichlorofluoromethane, dichlorodifluoromethane, dichlorotetrafluoromethane, monochlorodifluoromethane, trichlorotrifluoromethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 59 to 98% by weight of the composition, and can, in the absence of other cosmetic adjuncts, form the balance of the composition.

A wide variety of conventional sunscreening agents, such as those described in U.S. Pat. No. 4,919,934 to Deckner et al. hereby incorporated by reference, may also be used in the cosmetic compositions of the invention.

Such agents include, for example, p-aminobenzoic acid, its salts and its derivatives, anthranilates, salicylates, cinnamic acid derivatives, di- and trihydroxy cinnamic acid derivatives, hydrocarbons such as diphenylbutadiene and stilbene, dibenzalacetone and benzalacetophenone, naphthasulfonates, di-hydroxy naphthloic acid and its salts, hydroxy diphenylsulfonates, coumarin derivatives, diazoles, quinine salts, quinoline derivatives, hydroxy or methoxy substituted benzophenones, uric or vilouric acid, tannic acid and its derivatives, hydroquinone, and benzophenones.

In a sixth embodiment of the invention, the surfactant may be used in a toothpaste composition such as is taught and is described in U.S. Pat. No. 4,935,227 to Duckworth, which is hereby incorporated by reference.

Such compositions generally comprise abrasive gels (e.g. calcium carbonate), oral therapeutic agents (e.g., flourine containing compound), coactives, flavoring agents, sweetening agents, humectants and binding or thickening gels.

Preferred toothpastes of this invention comprise 0 to 1.5% by weight of anionic surfactant. In more preferred products the amount of anionic surfactant is 0 to 1% by weight with most preferred amounts being 0 to 0.75% by weight.

Toothpastes of this invention may include other surfactants, especially non-ionic surfactants.

Toothpaste of the invention will also comprise the usual additional ingredients in particular humectant binder or thickening agent.

Humectants which may be used include glycerol, sorbitol syrup, polyethylene glycol, lactitol, xylitol or hydrogenated corn syrup. The total amount of humectant present will generally range from 10% to 85% by weight of the toothpaste.

Numerous binding or thickening agents have been indicated for use in toothpastes, preferred ones being sodium carboxymethylcellulose, cross-linked polyacrylates and xanthan gum. Others include natural gum binders such as gum tragacanth, gum karaya and gum arabic, Irish moss, alginates, and carrageenans. Silica thickening agents include the silica aerogels and various precipitated silicas. Mixtures of binders and thickeners may be used. The amount of binder and thickening agent included in a toothpaste is generally between 0.1 and 15% by weight.

A typical toothpaste composition may comprise (percentages by weight):

| Ingredients | % by Weight |
| --- | --- |
| Synthetic surfactants (sodium lauryl sulfate) | .01–3% |
| Surfactant of Invention | 1–10% |
| Alkyl or aryl sulfate or sulfonate | 0–1% |
| Abrasive (e.g., silic acid/ $CaCO_3$) | 20–55% |
| Active ingredients (e.g., Pyrophosphates) | 0.1–2% |
| Humectant (glycerin, sorbitol) | 10–45% |
| Thickeners (cellulose derivatives) | 0–3% |
| Sequestering agents (e.g. citrate) | 0.1–0.4% |
| Flavoring agents | 0.5–2% |
| Sweeteners | 0–0.5% |
| Dye stuff | 0–0.1% |
| Water | Balance |

In a seventh embodiment of the invention, the molecule of the invention may be used in a light duty liquid detergent composition such as those taught in U.S. Pat. No. 4,671,894 to Lamb et al. U.S. Pat. No. 4,368,146 to Aronson et al. and U.S. Pat. No. 4,555,366 to Bissett et al., all of which are hereby incorporated by reference into the subject application.

Generally such compositions comprise a mixture of sulphate and sulphonate anionic surfactants together with a suds stabilizing agent. These compositions may also comprise nonionic surfactants designed to reduce the level of non-performing ingredients such as solvents and hydrotropes and zwitterionic surfactants for providing enhanced grease and particulate soil removal performance.

Among other ingredients which may also be used in such compositions are opacifiers (e.g. ethylene glycol distearate), thickeners (e.g., guar gum), antibacterial agents, antitarnish agents, heavy metal chelators (e.g. ETDA), perfumes and dyes.

A typical light duty liquid composition maly comprise (all percentages by weight):
(a) 0.01–65% anionic;
(b) b 0.01–50% surfactant of invention;
(c) 0–8% suds producing agent (e.g. alkyl alcohol amide);
(d) 0–10% hydrotrope (e.g., benzene sulfonate); and
(e) minors plus water to 100%.

In an eighth embodiment of the invention the molecule of the invention may be used in underarm deodorant/antiperspirant compositions such as those taught in U.S. Pat. No. 4,919,934 to Deckner, U.S. Pat. No. 4,944,937 to McCall and U.S. Pat. No. 4,944,938 to Patini, all of which patents are hereby incorporated by reference.

Such compositions generally comprise a cosmetic stick (gel or wax) composition which in turn generally comprises one or more liquid base materials (e.g., water, fatty acid and fatty alcohol esters, water-insoluble ethers and alcohols, polyorganosiloxanes); a solidifying agent for solidifying the liquid base; and an active component such as bacteriostats or fungistats (for antideodorant activity) or astringent metallic salts (for antiperspirant activity).

These compositions may also comprise hardeners, strenghteners, emollients, colorants, perfumes, emulsifiers and fillers.

EXAMPLE 1

Synthesis of 3-(octyloxy)-2-hydroxypropyl-β-D-galactopyranoside

Acetobromogalactose (2,3,4,6-tetra-O-acetyl-α-D-galactopyranosyl bromide) was mixed with allyl alcohol and mercuric cyanide via the Koenigs-Knorr glycosylation to obtain ally-β-D-galactopyranoside tetraacetate. This was followed by oxidation with 3-chloroperoxybenzoic acid in dichloromethane to obtain 2,3-epoxypropyl-β-D-galactopyranoside 2,3,4,6-0-tetraacetate (epoxide compound). To a solution of the above-identified epoxide compound (0.50 g, 1.24 mmoles) and 1-octanol (5-6 ml) was added 0.045 g of DDQ (2,3-dichloro-5,6-dicyano-1,4-benzoquinone). The reaction was run at 60°-70° C. under an inert atmosphere of nitrogen. Reaction was followed by thin layer chromatography in an eluent of 50/50 volume of ethyl acetate/hexane. The product had a Rf value of 0.6. After one day another 0.06 g of DDQ was added to the mixture. When the reaction was complete, the product (0.35 g) was isolated by column chromatography on 60 A (Merck) silica gel in a solvent system consisting of 50% ethyl acetate/50% hexane.

Deprotection was done using sodium methoxide in 35 ml of anhydrous methanol for 5-6 hours. Methanol was removed under reduced pressure. This crude product was further purified on a silica gel column (9:1 CHCl3, MeOH) to give the final product as a white solid (0.15 g) as seen below:

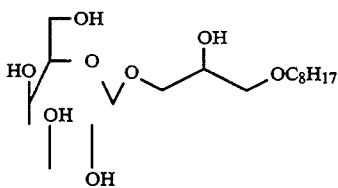

EXAMPLE 2

Synthesis of 3-dodecyloxy)-2-hydroxypropyl-β-D-galactopyranoside

The epoxide was obtained as described in Example 1. To a solution of the epoxide (1.20 g, 2.97 mmoles) and n-dodecanol (12 ml) was added 0.55 g of DDQ. The temperature was raised to 80°-85° C. and the reaction was monitored by TLC. After 3 days the starting epoxide was completely reacted.

The product was isolated by column chromatography on 60A (Merk) silica gel using a solvent system consisting of 50/50 v/v Hexane:ethyl acetate. The product had a Rf value of 0.65 and 1.06 g of a light caramel colored syrup was isolated (61% yield).

Deprotection was accomplished as in Example 1. The above product was dissolved in 50 ml of anhydrous methanol with a catalytic amount of sodium methoxide. The reaction was allowed to stir for 5-6 hours and subsequently treated with Bio-Rad cation exchange resin (AG 50W-X8 50-100 mesh). The resin was filtered off and methanol was removed under reduced pressure to afford a tacky solid. Addition of ether to the tacky solid gave a white precipitate (0.69 g, 91% yield).

EXAMPLE 3

Synthesis of 3-(hexadecyloxy)-2-hydroxypropyl-β-D-galactopyranoside

The epoxide was obtained as described in Example 1. The epoxide was reacted with 10 equivalents of hexadecanol and catalytic amounts of DDQ at 90°-100° C. under same conditions as for the dodecyl chain. Deacetylation and purification (same as Example 2) gave the final product

EXAMPLE 4

Alternative Syntheses of 3-(octyloxy)-2-hydroxypropyl-β-D-galactopyranoside

In a 25 ml two neck round bottom flask was added 0.80 q (1.98 mmoles) of 2,3-epoxypropyl-β-D-galactopyranoside 2,3,4,6-0-tetraacetate and 4.0 equivalents of 1-octanol. The reaction mixture was cooled to −10° C. followed by addition of 0.034 equivalent of a 1.0M solution of SnCl4 in dichloromethane. The reaction was allowed to warm up to room temperature over a period of one hour, and then heated to a temperature of 45° C. for 12-14 hours. Column chromatography was used to purify the product. The excess octanol was initially isolated using a 9:1 hexane/ethyl acetate eluent. Subsequent elution with 1:1 hexane/ethyl acetate gave 0.55 g of a clear syrupy material (52% yield). $^1$H NMR and MS showed identical spectra to the DDQ reaction product. Deprotection (same as Example 1) gave 0.36 g (95% yield) of final product.

SURFACTANCY

In order to determine the effectiveness of these compounds as surfactant, various physical properties (i.e., CMC, Krafft point, foam height, detergency) are tested relative to other known surfactants. These results are discussed in Examples 5 to 9 below.

EXAMPLE 5

Critical Micelle Concentration (CMC)

The CMC is defined as the concentration of a surfactant at which it begins to form micelles in solution. Specifically, materials that contain both a hydrophobic group and a hydrophilic group (such as surfactants) will tend to distort the structure of the solvent (i.e., water) they are in and therefore increase the free energy of the system. They therefore concentrate at the surface, where, by orienting so that their hydrophobic groups are directed away from the solvent, the free energy of the solution is minimized. Another means of minimizing the free energy can be achieved by the aggregation of these surface-active molecules into clusters or micelles with their hydrophobic groups directed toward the interior of the cluster and their hydrophilic groups directed toward the solvent.

The value of the CMC is determined by surface tension measurements using the Wilhemy plate method or Du Nuey ring method. While not wishing to be bound by theory, it is believed that a low CMC is a measure of surface activity (i.e., lower CMC of one surfactant versus another indicates the surfactant with lower CMC is more surface active). In this regard, it is believed that lower CMC signifies that lesser amounts of a surfactant are required to provide the same surfactancy benefits as a surfactant with higher CMC.

The CMC of 3-(dodecyloxy)-2-hydroxypropyl-$\beta$-D-galactopyranoside was measured at $1.23 \times 10^{-4}$M at 25° C. The CMC of n-$C_{12}$ alcohol with 7 ethoxylated units (from Neodol ™ surfactants ex Shell) is $7.3 \times 10^{-5}$M [40° C.]. This indicates that the surfactants of the invention are comparable to other well-known commercially available surfactants.

EXAMPLE 6

Krafft Points

The temperature at and above which surfactants begin to form micelles is referred to as Krafft point (Tk) and at this temperature the solubility of a surfactant becomes equal to its CMC.

Krafft point was measured by preparing a 1% dispersion of the surfactant in water. If the surfactant was soluble at room temperature, the solution was cooled to 0° C. When the surfactant did not precipitate out, its Krafft point was considered to be <0° C. If it precipitated out, the solution was slowly warmed with stirring in a water bath. The temperature at which the precipitate dissolved was determined to be the Krafft point.

If the Krafft point was above room temperature, the solution was first heated rapidly to dissolve all the surfactant. It was then cooled until precipitation occurred, and was then slowly warmed to determine the Krafft point described above.

While not wishing to be bound by theory, it is believed that lower Krafft points are indicative of a surfactant being more soluble in aqueous system. Also, since micelles exist only at temperature above Tk, surfactants with high Tk will show lower activity at low temperatures. Finally, it is believed that surfactants with lower Krafft points are easier to formulate in multi-electrolyte systems because of their greater tolerance to salt.

The Krafft point of 3-(dodecyloxy)-2-hydroxypropyl-$\beta$-D-galactopyranoside has been measured at about less than 8° C. This Krafft point is another good indication of surfactant activity.

EXAMPLE 7

Foam Height

Foam is an important attribute in many consumer products. Foam is one of the dominant factors that determines the commercial value of products such as shampoo, soap, etc. Also, acceptability of many consumer products is closely related to the quality and texture of the foam they produce (psychological aspect).

Since most of the foaming data on surfactants is typically obtained by the Ross-Miles method (Ross, J. and Miles, G. D., Am. Soc. for Testing Material Method D1173-53 Philadelphia, PA. [1953]; Oil & Soap [1958]62:1260) the foaming ability of these surfactants was also acquired using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette (initial foam height) and then again after a given amount of time.

Using this method, the foam production (measured initially) and foam stability (the height after 10 minutes) are reported. All of the foaming was achieved at 45° C. in water with 120 ppm hardness. The foam height is represented in millimeters (mm).

The initial foam height and height after 10 minutes (i.e. foam stability) was measured for 3-(dodecyloxyl)-2-hydroxypropyl-$\beta$-D-galactopyranoside (DHG) and for a common surfactant, sodium dodecyl sulfonate (SDS) and results set forth below:

|     | Initial Height | After 10 Minutes |
| --- | --- | --- |
| DHG | 135 | 124 |
| SDS | 153 | 144 |

As seen from this data, the foaming ability of DHG is comparable to that of other well-known, commercially available surfactants.

EXAMPLE 8

The detergency of the surfactants of the invention was measured by recording the % triolein (a grease substance) removed (as an absolute value) from polyester using 3-(dodecyloxy)-2-hydroxypropyl-$\beta$-D-galactopyranoside (DHG) alone or in combination with a $C_{12}$ nonionic surfactant with three alkoxylated groups.

More particularly, the amount of soil removed was evaluated using $^3$H ratio-labelled triolein. Following the wash, $4 \times 1$ ml samples of wash liquor were removed from each pot and the activity determined using a liquid scintillation counter. Percentage detergencies were calculated from the relationship.

$$\% \text{ detergency} = \frac{Aw \times 100}{As}$$

Aw=total activity in wash liquor As=level of activity originally applied to cloth Using these methods, the following results were obtained:

| | % Detergency Based on Various Ratios of DHG to $C_{12}E_3$* | | | | | |
| --- | --- | --- | --- | --- | --- | --- |
| | 100% DHG | 80/20 | 60/40 | 40/60 | 20/80 | 100% $C_{12}E_3$ |
| Detergency | 55% | 57% | 72% | 50% | 10% | 2% |

*Temperature 40° C., pH 10.7, Dose 1 g/$1^{-1}$, 0.05M (NaBO$_2$4H$_2$O)

First, it should be noted that anything above 45% detergency is considered adequate detergency. From this, it can be seen that use of DHG alone (55% detergency) provides very good surfactancy on grease staining.

In addition, it can be seen that, when DHG is used in combination with cosurfactant, optimum benefits are obtained at a range of about 20-60% cosurfactant. At levels beyond about 65% cosurfactant, the detergency effect of the DHG is minimized.

While not wishing to be bound by theory, it should also be noted that, since the surfactants used in the composition of the invention have relatively high hydrophilic-lipophilic balance, in formulating detergent composition, optimal synergistic detergency affects with cosurfactants should occur when using cosurfactants having a lower hydrophilic-lipophilic balance.

EXAMPLE 9

In Example 8, applicants tested detergency by combining the compounds of the invention with low alkoxylated (i.e., about 3EO) nonionic surfactant. The use of the compounds of the invention allows less alkoxylated nonionic to be used (i.e., provides an alternative).

The Krafft Temperature of DHPG is set forth below:
Krafft Temperature:8° C.

Figure 2:
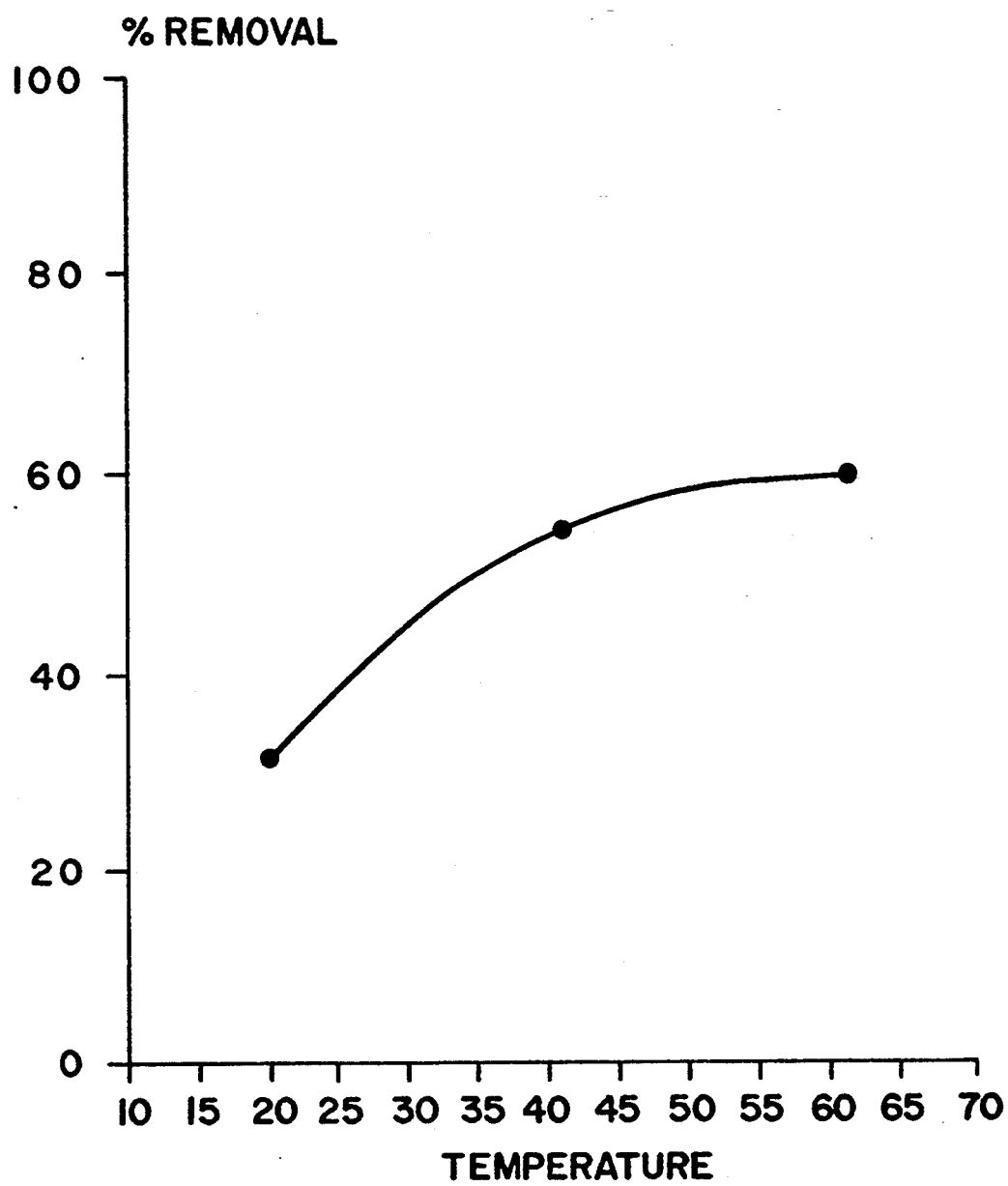
FIG. 2 is a graph showing triolein removal in a 20°–60° C. temperature range.

The detergency performance of DHPG, in triolein removal experiments at 40° C., with varying ratios of triethylene glycol mono-dodecyl ether ($C_{12}EO_8$) and octaethylene glycol mono-dodecyl ether are shown in FIG. 1. DHPG on its own gives triolein removal of 55% which is comparable to $C_{12}EO_8$ alone. Mixtures of DHPG and $C_{12}EO_3$ give a synergistic maximum is observed of 72% triolein removal. As expected mixtures of DHPG and $C_{12}EO_8$ give no marked difference in detergency compared to the single surfactants. FIG. 2 shows the influence of temperature on triolein removal for DHPG alone; below 40° C. triolein removal decreases sharply, and above 40° C. it appears to plateau at 60% removal.

DHPG by itself was found to exhibit effective triolein removal (about 55%), which is comparable to $C_{12}EO_8$. In combination with $C_{12}EO_3$ synergistic triolein removal of 72% is achieved. For DHPG alone triolein removal is dependent on temperature; below 40° C. triolein removal decreases sharply, and above 40° C. it appears to plateau at 60% removal. It also exhibits good foaming properties.

The detergency efficacy of DHG (55% triolein removal when used alone) was comparable to $C_{12}EO_8$.

It should also be noted that detergency is affected by temperature at which it is conducted. Thus, while detergency by DHG alone at 40° C. was 55% triolein removal (Example 8), below 40° C., triolein removal decreases sharply and, above 40° C., it appears to plateau at 60% removal.

We claim:

1. A liquid detergent composition comprising (percentages by weight):
   (a) 5–70% of a detergent active mixture wherein said mixture comprises a glyceroglycolipid compound having the structure:

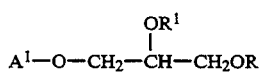

wherein $A^1$ comprises one to four saccharide units, R and $R^1$ are the same or different and are hydrogen, a straight or branched-chain saturated or unsaturated hydrocarbon radical having from about 1 to about 24 carbons or an acyl group; except that R and $R^1$ cannot both be hydrogen; and wherein said mixture further comprises one or more additional actives selected from the group consisting of alkali metal or alkanolamine soap, 0 to 24 carbon fatty acid soap, nonionic surfactants, cationic surfactants, zwitterionic surfactants and amphoteric surfactants;
   (b) 0–50% builder;
   (c) 0–40% electrolyte;
   (d) 0.01–5% enzyme;
   (e) 0.1–15% enzyme stabilizer;
   (f) 0–20% phase regulant; and (g) remainder water and minors.

2. A powder detergent composition comprising (percentages by weight):
   (a) 5 to 40% of a detergent active mixture wherein said mixture comprises a glyceroglycolipid having the structure:

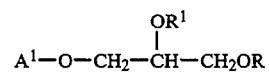

wherein $A^1$ comprises one to four saccharide units, R and $R^1$ are the same or different and are hydrogen, a straight or branched-chain saturated or unsaturated hydrocarbon radical having from about 1 to about 24 carbons or an acyl group; except that R and $R^1$ cannot both be hydrogen; and wherein said mixture further comprises one or more additional actives selected from the group consisting of alkali metal or alkanolamine soap, 0 to 24 carbon fatty acid soap, nonionic surfactants, cationic surfactants, zwitterionic surfactants and amphoteric surfactants;
   (b) 0–40% builder;
   (c) 0–30% buffer salt;
   (d) 0–30% sulfate;
   (e) 0–20% bleach system;
   (f) 0–4% enzyme; and
   (g) minors plus water to 100%

3. A toilet bar composition comprising:

| Ingredients | % by Weight |
| --- | --- |
| $C_8[-]$ to $C_{24}$ fatty acid | 5–60% |
| Glyceroglycolipid mixture of claim 1 | 1–45% |
| Alkyl or aryl sulfate or sulfonate | 0–5% |
| [Coactive other than glyceroglycolipid] | 0–50% |
| Surfactant other than glyceroglycolipid selected from the group consisting of soap; anionic other than alkyl or aryl sulfate or sulfonate; nonionic; zwitterionic; amphoteric; and mixtures thereof | |
| Sorbitol | 0.1–10% |
| Cellulose | 0–10% |
| Sequestering agent | 0.1–0.5% |
| Water and minors | to Balance.-- |

4. A facial body cleanser composition comprising the following:

| Ingredients | % by Weight |
| --- | --- |
| $C_8$–$C_{24}$ fatty acid salt | 1–45% |
| Glyceroglycolipid mixture of claim 1 | 10–75% |
| Alkyl sulfate | 0–20% |
| Cocamidobetaine | 1–15% |
| Sorbitol | 0.1–15% |
| Refattying alcohol | 0.5–5% |
| Water soluble polymer | 0–10% |
| Thickener | 0–15% |
| Quaternized cellulose | 0–0.5% |
| Citrate | 0.1–0.4% |
| Water and minors | to Balance. |

5. A shampoo composition comprising:
   (1) 5–15% glyceroglycolipid mixture of claim 1;
   (2) 0–10% anionic surfactant;
   (3) 0–10% amphoteric surfactant;
   (4) 0–5% lauramide MEA;

(5) 0–5% thickener
(6) 0–2% fragrance
(7) 0–1% preservative; and
(8) remainder water.

6. A conditioner composition comprising: (percentages by weight)
(a) 1–98% glyceroglycolipid of claim 1 or surfactant mixture comprising glyceroglycolipid mixture of claim 1;
(b) 0–80% builder;
(c) 0–10% chelating agent;
(d) 0–5% soil release agent;
(e) 0–5% antiredeposition agent;
(f) 0–2% enzymes;
(g) .1–20% conditioning agent;
(h) 0.1–10% stabilizer for conditioner;
(i) water and minors to 100%.

7. A toothpaste composition comprising:

| Ingredients | % by Weight |
| --- | --- |
| Synthetic surfactants | .01–3% |
| Glyceroglycolipid mixture of claim 1 | 1–10% |
| Alkyl or aryl sulfate or sulfonate | 0–1% |
| Abrasive | 20–55% |
| Pyrophosphate | 0.1–2% |
| Humectant | 10–45% |
| Thickeners | 0–3% |
| Sequestering agents | 0.1–0.4% |
| Flavoring agents | 0.5–2% |
| Sweeteners | 0–0.5% |
| Dye stuff | 0–0.1% |
| Water | Balance. |

8. A light duty liquid composition comprising: percent by weight
a) 0.01–65% anionic surfacant;
(b) 0.01–50% glyceroglycolipid mixture of claim 1
(c) 0–8% suds producing agent;
(d) 0–10% hydrotrope; and
(e) minors plus water to 100%, 9. A composition according to claim 1, wherein A′ is a monosaccharide, R′ is hydrogen and R is a straight-chained hydrocarbon radical having 6 to 18 carbons.

10. A composition according to claim 9, wherein the monosaccharide is galactoside.

11. A composition according to claim 9, wherein R is an alkyl group having 12 carbons.

12. A composition according to claim 2, wherein A′ is a monosaccharide, R′ is hydrogen and R is a straight-chained hydrocarbon radical having 6 to 18 carbons.

13. A composition according to claim 12, wherein the monosaccharide is galactoside.

14. A composition according to claim 12, wherein R is an alkyl group having 12 carbons.

* * * * *